(12) United States Patent
Dryer et al.

(10) Patent No.: US 7,655,046 B2
(45) Date of Patent: Feb. 2, 2010

(54) EXPANDABLE SPINAL FUSION CAGE AND ASSOCIATED INSTRUMENTATION

(75) Inventors: Randall F. Dryer, Austin, TX (US); Bret M. Berry, Sandy, UT (US); Eric C. Lange, Collierville, TN (US)

(73) Assignee: Warsaw Orthopedic, Inc.

( * ) Notice: Subject to any disclaimer, the term of this patent is extended or adjusted under 35 U.S.C. 154(b) by 312 days.

(21) Appl. No.: 11/335,261

(22) Filed: Jan. 19, 2006

(65) Prior Publication Data
US 2006/0206207 A1    Sep. 14, 2006

Related U.S. Application Data

(60) Provisional application No. 60/645,299, filed on Jan. 20, 2005.

(51) Int. Cl.
*A61F 2/44* (2006.01)
(52) U.S. Cl. ............... 623/17.15; 623/17.11; 623/17.16
(58) Field of Classification Search .................. 606/61, 606/246, 279; 623/17.11–17.16
See application file for complete search history.

(56) References Cited

U.S. PATENT DOCUMENTS

| | | | |
|---|---|---|---|
| 4,878,915 A | | 11/1989 | Brantigan |
| 5,059,193 A | | 10/1991 | Kuslich |
| 5,360,450 A | * | 11/1994 | Giannini ................... 623/21.19 |
| 5,443,514 A | * | 8/1995 | Steffee ......................... 128/898 |
| 5,554,191 A | * | 9/1996 | Lahille et al. ............. 623/17.11 |
| 5,593,409 A | | 1/1997 | Michelson |
| 5,653,763 A | | 8/1997 | Errico et al. |
| 5,658,336 A | * | 8/1997 | Pisharodi .................. 623/17.16 |
| 5,683,463 A | * | 11/1997 | Godefroy et al. .......... 623/17.16 |
| 5,865,848 A | | 2/1999 | Baker |
| 5,888,224 A | * | 3/1999 | Beckers et al. ............ 623/17.16 |
| 6,117,174 A | | 9/2000 | Nolan |
| 6,129,763 A | | 10/2000 | Chauvin et al. |
| 6,217,579 B1 | | 4/2001 | Koros |
| 6,332,895 B1 | | 12/2001 | Suddaby |

(Continued)

FOREIGN PATENT DOCUMENTS

DE    40 12 622    7/1991

(Continued)

*Primary Examiner*—Thomas C Barrett
*Assistant Examiner*—Andrew Yang

(57) ABSTRACT

An expandable spinal implant comprising a cage body including at least two movable branches having first end portions that are interconnected to one another and second end portions that are movable relative to one another. The movable branches include a first shell portion having a first pair of longitudinal edges and defining a first hollow region therebetween, and a second shell portion having a second pair of longitudinal edges and defining a second hollow region therebetween, with the first and second hollow regions cooperating to define at least a portion of a hollow interior of the cage body. An expansion member co-acts with the first and second shell portions to transition the cage body to an expanded configuration as the expansion member is axially displaced along said first and second pairs of longitudinal edges. In one embodiment, at least one of the shell portions defines a plurality of retention elements positioned at select axial locations along a corresponding one of the longitudinal edges, with the expansion member engaged with one or more of the retention elements to retain the expansion member at a select axial position to maintain the implant in the expanded configuration.

27 Claims, 7 Drawing Sheets

U.S. PATENT DOCUMENTS

| | | |
|---|---|---|
| 6,371,989 B1 | 4/2002 | Chauvin et al. |
| 6,436,140 B1 * | 8/2002 | Liu et al. .................. 623/17.11 |
| 6,436,142 B1 | 8/2002 | Paes et al. |
| 6,451,057 B1 | 9/2002 | Chen et al. |
| 6,454,807 B1 | 9/2002 | Jackson |
| 6,471,724 B2 * | 10/2002 | Zdeblick et al. .......... 623/17.16 |
| 6,491,724 B1 | 12/2002 | Ferree |
| 6,500,205 B1 | 12/2002 | Michelson |
| 6,955,691 B2 * | 10/2005 | Chae et al. ............... 623/17.16 |
| 7,118,598 B2 * | 10/2006 | Michelson ............... 623/17.11 |
| 7,220,280 B2 * | 5/2007 | Kast et al. ................ 623/17.11 |
| 2002/0040243 A1 | 4/2002 | Attali et al. |
| 2002/0116006 A1 * | 8/2002 | Cohen ......................... 606/99 |
| 2002/0116066 A1 * | 8/2002 | Chauvin et al. .......... 623/17.16 |
| 2002/0143401 A1 * | 10/2002 | Michelson ............... 623/17.16 |
| 2002/0161444 A1 | 10/2002 | Choi |
| 2006/0058876 A1 * | 3/2006 | McKinley ................ 623/17.11 |
| 2006/0085067 A1 * | 4/2006 | Gradel et al. ............ 623/17.11 |

FOREIGN PATENT DOCUMENTS

| | | |
|---|---|---|
| DE | 44 16 605 C1 | 6/1995 |
| EP | 0 635 246 | 1/1995 |
| WO | WO 00/12033 | 3/2000 |

* cited by examiner

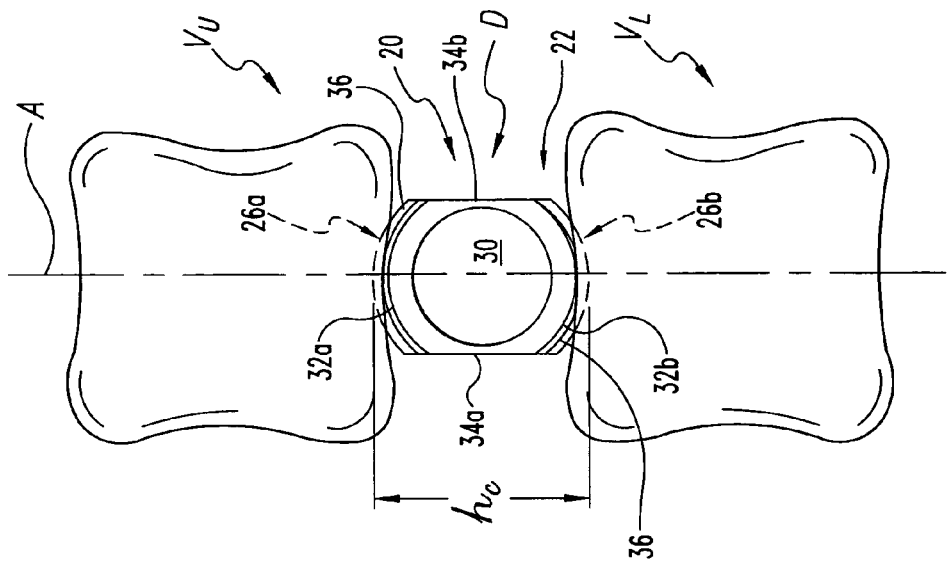
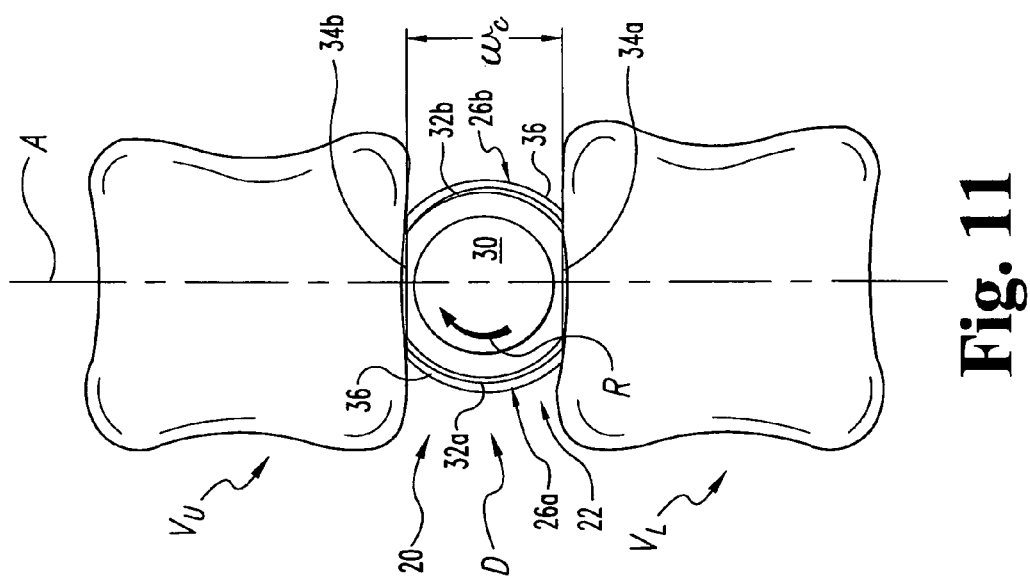
Fig. 11
Fig. 12

EXPANDABLE SPINAL FUSION CAGE AND ASSOCIATED INSTRUMENTATION

CROSS REFERENCE TO RELATED APPLICATIONS

The present application claims the benefit of U.S. Provisional Patent Application Ser. No. 60/645,299 filed on Jan. 20, 2005, the contents of which are hereby incorporated by reference in their entirety.

FIELD OF THE INVENTION

The present invention relates generally to the field of spinal implants, and more particularly relates to an expandable spinal fusion cage and associated instrumentation.

BACKGROUND

There have been numerous attempts to develop a spinal implant to replace a damaged or degenerated natural spinal disc and to maintain sufficient stability of the disc space between adjacent vertebrae, at least until arthrodesis is achieved. These types of spinal implants have taken many forms.

For example, spinal implants can either be solid, sometimes referred to as a spacer or plug, or can define a hollow interior designed to permit bone in-growth, sometimes referred to as a fusion device or fusion cage. The interior of a fusion device may be filled with a bone growth inducing substance to facilitate or promote bone growth into and through the device. It is commonly accepted that spinal implants that facilitate or promote natural bone in-growth typically achieve a more rapid and stable arthrodesis. Some spinal implant designs are inserted into the disc space via a threading technique, while other designs are inserted into the disc space via a push-in or impaction technique.

One area that is usually not addressed by the above-discussed spinal implant designs concerns maintaining and restoring the natural anatomy of the fused spinal segment. Notably, once natural disc material is removed, the normal lordotic or kyphotic curvature of the spine is reduced or eliminated. With regard to prior spinal implants having a substantially uniform height, the need to restore this curvature is largely neglected. Additionally, in some cases, the adjacent vertebral bodies are reamed to form a passage having a shape corresponding to the particular shape of the spinal implant. In other cases, the normal curvature is established prior to reaming followed by insertion of the spinal implant. However, these techniques generally involve over-reaming of the posterior portion of the adjacent vertebral bodies, thereby resulting in excessive removal of load bearing vertebral bone which may lead to instability of the portion of the spinal column being treated. Also, it is typically difficult to ream through the posterior portion of the lower lumbar segment where lordosis is the greatest. As a result, limited effort or in some cases no effort has been made to restore the lordotic curvature. Consequently, a spinal curvature deformity may form as the vertebral bodies settle around the spinal implant.

Thus, there is a general need in the industry to provide an improved spinal implant and associated instrumentation. The present invention satisfies this need and provides other benefits and advantages in a novel and unobvious manner.

SUMMARY

The present invention relates generally to a spinal implant and associated instrumentation. While the actual nature of the invention covered herein can only be determined with reference to the claims appended hereto, certain forms of the invention that are characteristic of the preferred embodiments disclosed herein are described briefly as follows.

In one form of the present invention, a spinal fusion cage is provided that is transitionable from an initial configuration to an expanded configuration via displacement of an expansion member between two or more branch portions of the fusion cage.

In another form of the present invention, instrumentation is provided for inserting a spinal fusion cage into an intervertebral opening and for transitioning the fusion cage from an initial configuration to an expanded configuration via displacement of an expansion member between two or more branch portions of the fusion cage.

In another form of the present invention, a method is provided for inserting a spinal fusion cage into an intervertebral opening and for transitioning the fusion cage from an initial configuration to an expanded configuration via displacement of an expansion member between two or more branch portions of the fusion cage.

It is one object of the present invention to provide an improved spinal implant and instrumentation associated therewith. Further objects, features, advantages, benefits, and aspects of the present invention will become apparent from the drawings and description contained herein.

BRIEF DESCRIPTION OF THE DRAWINGS

FIG. 11 is a coronal plane view of the expandable fusion cage assembly illustrated in FIG. 1, as shown in a first orientation with the flat side walls of the fusion cage arranged generally parallel with the endplates of the adjacent vertebrae.

FIG. 12 is a coronal plane view of the expandable fusion cage assembly illustrated in FIG. 1, as shown in a second

DESCRIPTION OF THE PREFERRED EMBODIMENTS

Figure 1:
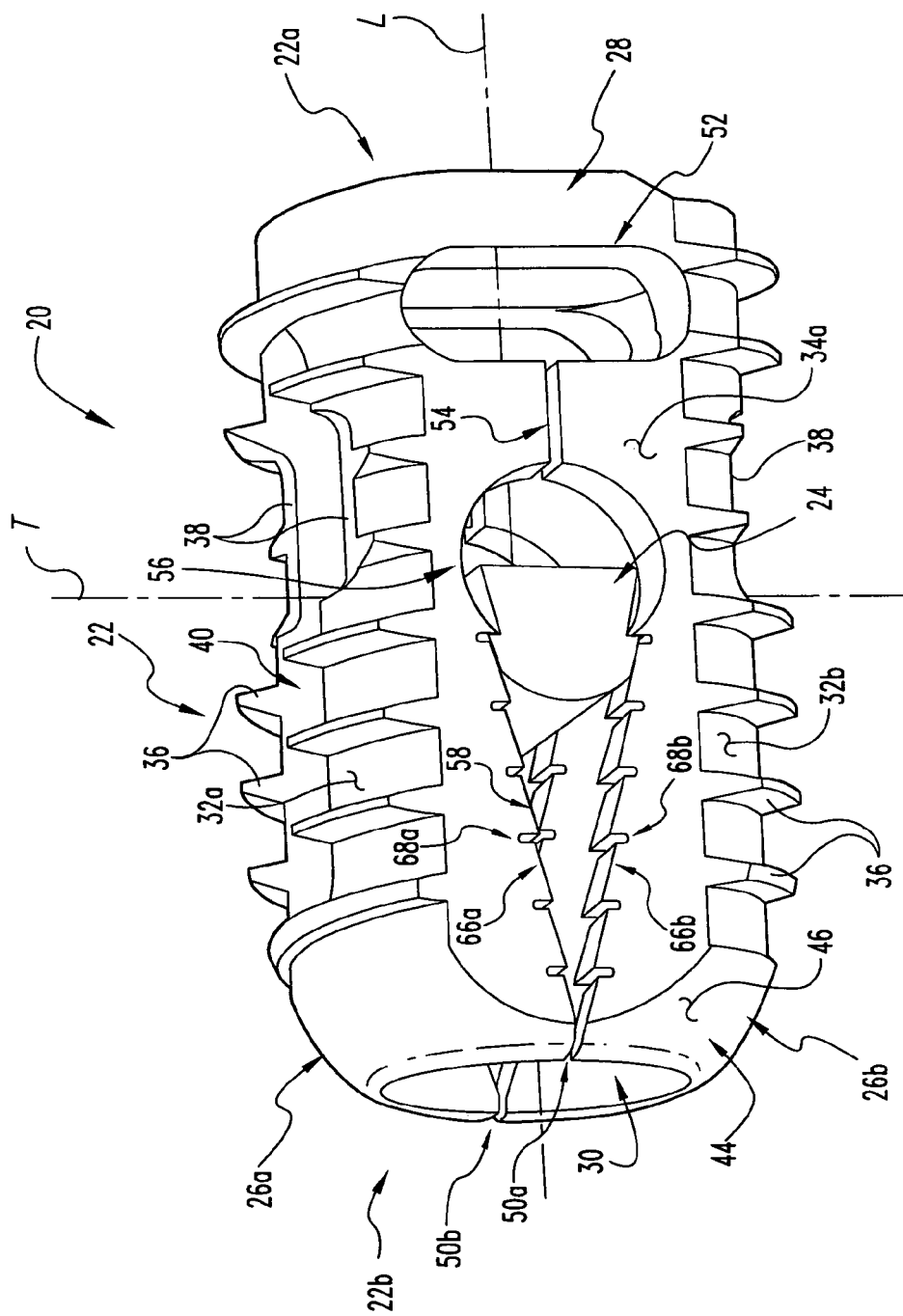
FIG. 1 is a side perspective view of an expandable fusion cage assembly according to one form of the present invention.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

Figure 10:
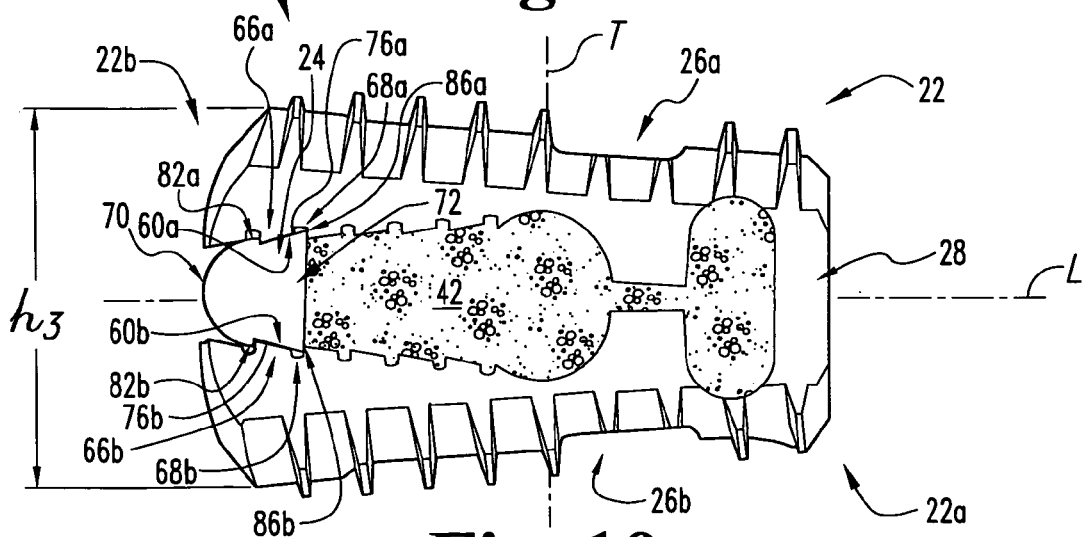
FIG. 10 is a side view of the expandable fusion cage assembly illustrated in FIG. 1, as shown in a fully-expanded configuration with the expansion member disposed at a third operational position within the fusion cage.

Referring to FIG. 1, shown therein is a spinal implant assembly 20 according to one form of the present invention. The spinal implant 20 extends along a longitudinal axis L and is generally comprised of an expandable fusion cage 22 and an expansion member 24. As will be discussed below, the expansion member 24 serves to transition the fusion cage 22 from an initial configuration (FIGS. 1 and 8) toward an expanded configuration (FIG. 10). As will also be discussed below, in the illustrated embodiment of the invention, expansion of the fusion cage 22 occurs along a transverse axis T so as to distract the disc space and/or to restore or maintain lordosis between the adjacent vertebral bodies. However, it should be understood that in other embodiments of the invention, expansion of the fusion cage 22 may occur in multiple directions and along multiple axes.

The components of the spinal implant assembly 20 are each preferably formed of a biocompatible material. In one embodiment, the material used to form the fusion cage 22 and/or the expansion member 24 is a medical grade metallic material, such as, for example, titanium. However, the use of other metallic materials are also contemplated, including stainless steel and stainless steel alloys, titanium and titanium alloys, shape-memory alloys, cobalt chrome alloys, or any combination of these metallic materials. Additionally, it should be understood that forming the fusion cage 22 and/or the expansion member 24 from a non-metallic material is also contemplated. For example, in another embodiment, the fusion cage 22 and/or the expansion member 24 may be formed of bone or bone substitute materials. In a further embodiment, the fusion cage 22 and/or the expansion member 24 may be formed of a resorbable material that resorbs or degrades within the body over a period of time so as to allow for partial or total replacement by bone. In a specific embodiment, the fusion cage 22 and/or the expansion member 24 may be formed of a polymeric material, including, for example, a non-resorbable polymer such as polyetheretherketone (PEEK) or a resorbable polymer such as polylactates (PLA). Examples of other suitable materials include composite polymers, non-reinforced polymers, carbon-reinforced polymer composites, carbon fiber, PMMA, calcium hydroxide, ceramics, polylactide, polyglycolide, tyrosine-derived polycarbonate, polyanhydride, polyorthoester, polyphosphazene, calcium phosphate, calcium hydroxide, hydroxyapatite, bioactive glass, or any combination of these materials.

Referring collectively to FIGS. 1-6, shown therein are further details regarding the expandable fusion cage 22. The fusion cage 22 includes a proximal end portion 22a and a distal end portion 22b. In one embodiment of the invention, the fusion cage 22 is generally comprised of a pair of movable branch portions 26a, 26b extending generally along the longitudinal axis L and interconnected to one another adjacent the proximal end portion 22b via a fixed base portion 28. However, it should be understood that the fusion cage 22 may define any number of branch portions, including three, four, or five or more branch portions. As will be discussed below, as the expansion member 24 is displaced relative to the fusion cage 22, the branch portions 26a, 26b will separate or splay apart to provide the fusion cage 22 with a cross sectional dimension adjacent the distal end portion 22b that is greater than the cross sectional dimension adjacent the proximal end portion 22a.

In the illustrated embodiment of the invention, the branch portions 26a, 26b are coupled to the fixed base portion 28 in such a manner as to allow the branch portions 26a, 26b to move relative to one another to provide for expansion of the fusion cage 22. In one embodiment, the branch portions 26a, 26b are formed integral with the base portion 28 to define a single-piece, unitary fusion cage 22. In this manner, the base portion 28 flexibly interconnects the branch portions 26a, 26b so as to allow for expansion of the fusion cage 22 via flexible material deformation of the branch portions 26a, 26b and/or the fixed base portion 28. The interconnection between the fixed base portion 28 and the branch portions 26a, 26b acts in a hinge-like manner during expansion of the fusion cage 22 to provide for substantially independent movement of the branch portions 26a, 26b.

Although the illustrated embodiment of the fusion cage 22 utilizes integrally connected branch portions 26a, 26b, it is also contemplated that the branch portions 26a, 26b may be formed separately and connected together to form a multi-piece fusion cage assembly. In another embodiment, the branch portions 26a, 26b may be pivotally attached to the base portion 28 or directly to one other via a hinge or pivot pin such that the fusion cage 22 may be expanded without relying on flexible material deformation. Other suitable means for coupling the branch portions 26a, 26b together to provide for expansion of the fusion cage 22 are also contemplated, including forming or coupling of the branch portions 26a, 26b directly to one another without the use of a fixed base portion 28.

In the illustrated embodiment of the invention, axial displacement of the expansion member 24 generally along the longitudinal axis L between the branch portions 26a, 26b causes the branch portions 26a, 26b to separate or splay apart, thereby expanding the fusion cage 22 along the transverse axis T. However, it should be understood that in other embodiments of the invention, rotational or pivotal displacement of the expansion member 24 relative to the branches 26a, 26b may cause the fusion cage 22 to expand. Other types of relative displacement between the expansion member 24 and the branch portions 26a, 26b are also contemplated for use in association with the present invention to expand the fusion cage 22, including, for example, displacement of the expansion member 24 in directions transverse to the longitudinal axis L.

Figure 6:
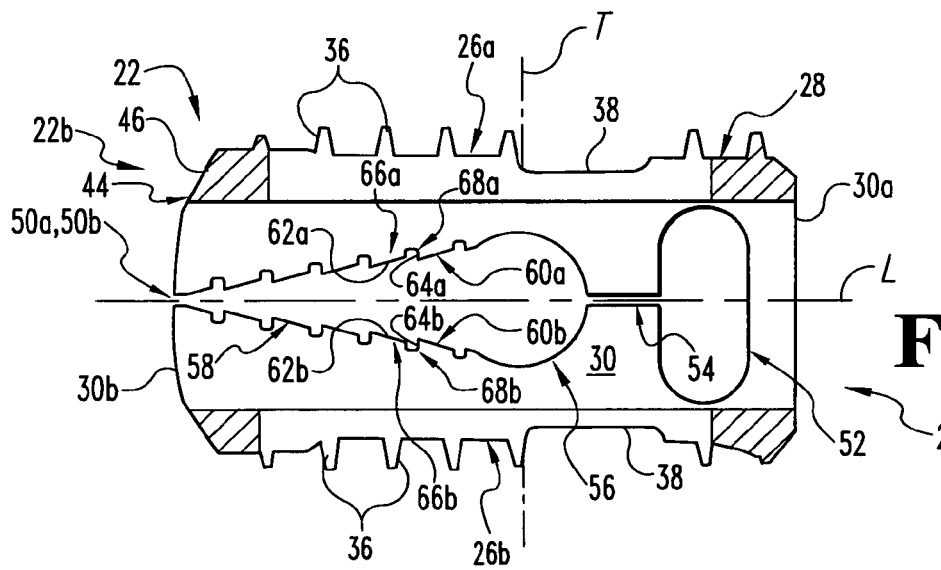
FIG. 6 is a cross-sectional side view of the fusion cage illustrated in FIG. 2, as taken along line 6-6 of FIG. 3.

In one embodiment of the invention, the branch portions 26a, 26b of the fusion cage 22 each have a shell-like configuration and cooperate with one another to define a substantially hollow cage interior or passage 30 extending generally along the longitudinal axis L. As illustrated in FIG. 6, the walls of the branch portion 26a, 26b are relatively thin so as to maximize the volume of hollow interior 30. As will be discussed below, maximizing the volume of hollow interior 30 will increase the amount of a bone growth promoting material that may be positioned within the fusion cage 22 to facilitate fusion with the adjacent vertebral bodies.

As illustrated in FIG. 6, the hollow interior or passage 30 preferably extends entirely through the fusion cage 22 so as to define a proximal opening 30a adjacent the proximal end 22a and a distal opening 30b adjacent the distal end 22b. However, it should be understood that in other embodiments of the invention, the hollow interior or passage 30 need not necessarily extend entirely through the fusion cage 22. In another embodiment, the branch portions 26a, 26b cooperate with one another to define a substantially cylindrical configuration. However, it should be understood that other shapes and configurations of the fusion cage 22 are also contemplated as falling within the scope of the present invention.

In the illustrated embodiment of the invention, the branch portions 26a, 26b define a first pair of oppositely-disposed outer surfaces 32a, 32b having a curved or arcuate configuration, and a second pair of oppositely-disposed outer surfaces 34a, 34b extending between the first pair of surfaces 32a, 32b and having a generally flat or planar configuration. In this embodiment of the fusion cage 22, the branch portions 26a, 26b cooperate with one another to define a substantially cylindrical configuration having truncated side portions. However, it should be understood that other shapes and configurations of the fusion cage 22 and the branch portions 26a, 26b are also contemplated as falling within the scope of the present invention, including, for example, a non-truncated cylindrical configuration, an elliptical configuration, a conical configuration, a rectangular configuration, or any other suitable shape or configuration.

The first pair of outer surfaces 32a, 32b preferably defines a number of bone anchoring elements 36 adapted for engagement with the adjacent vertebral bodies $V_U$, $V_L$ to prevent or inhibit movement of the fusion cage 22 once implanted within the intervertebral disc space D (FIG. 12). In a specific embodiment, the bone anchoring elements 36 comprise external threads extending along a substantial portion of the length of the fusion cage 22. The external threads preferably define a thread pattern that allows for threading advancement of the fusion cage 22 between the vertebral bodies $V_U$, $V_L$ as the fusion cage 22 is rotated about the longitudinal axis L. The threads also provide secure anchoring to the adjacent vertebral bodies $V_U$, $V_L$ subsequent to insertion into the intervertebral disc space D. Either or both of outer surfaces 32a, 32b may define a flattened region or recessed area 38 adjacent the proximal half of the fusion cage 22 which interrupts the external threads 36. The flattened region or recessed area 38 is included to provide additional flexibility to the branch portions 26a, 26b to facilitate expansion of the fusion cage 22 and/or to provide an external area of engagement with an instrument or tool.

Although the bone anchoring elements 36 have been illustrated and described as comprising external threads, it should be understood that other types and configurations of bone anchoring elements are also contemplated for use in association with the fusion cage 22. For example, various types and configurations of projections or surface irregularities may be provided which extend from the first pair of outer surfaces 32a, 32b, including ridges, teeth, spikes, surface roughening, or any other suitable anchoring element. Further, although the bone anchoring elements 36 are illustrated as extending about the fusion cage 22 in a circumferential direction, in other embodiments of the invention, the bone anchoring elements 36 may be configured to extend generally along the length of the fusion cage 22 in an axial direction. Additionally, it should also understood that in other embodiments of the invention, the first pair of outer surface 32a, 32b need not necessarily include bone anchoring elements 36, but may alternatively define a substantially smooth configuration devoid of any projections or surface irregularities. It should also be understood that although the second pair of outer surface 34a, 34b of the fusion cage 22 are illustrated as being devoid of any projections or surface irregularities, in other embodiments of the invention, the outer surfaces 34a, 34b may also define a number of bone anchoring elements.

In the illustrated embodiment of the fusion cage 22, each of the branch portions 26a and 26b defines at least one bone in-growth opening or window 40 extending through the outer surfaces 32a and 32b, respectively, and communicating with the hollow cage interior 30. The openings 40 are provided to permit bone growth from the adjacent vertebral bodies $V_U$, $V_L$ and into and potentially through the fusion cage 22. Although the fusion cage 22 is illustrated as including a single bone in-growth opening 40 extending through each of the outer surfaces 32a, 32b, it should be understood that in other embodiments, multiple bone in-growth openings 40 may extend through each of the outer surfaces 32a, 32b in communication with the hollow interior 30. It should further be understood that although the openings 40 are illustrated and described as communicating with the hollow interior 30, in other embodiments, the openings 40 need not necessarily extend entirely through the branch portions 26a, 26b.

Figure 3:
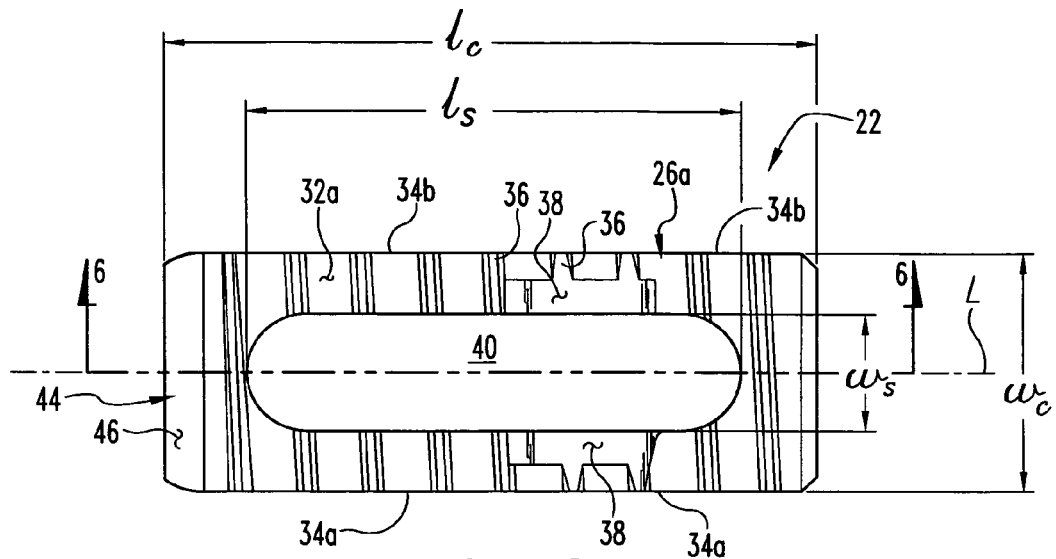
FIG. 3 is a top view of the fusion cage illustrated in FIG. 2.
Figure 2:
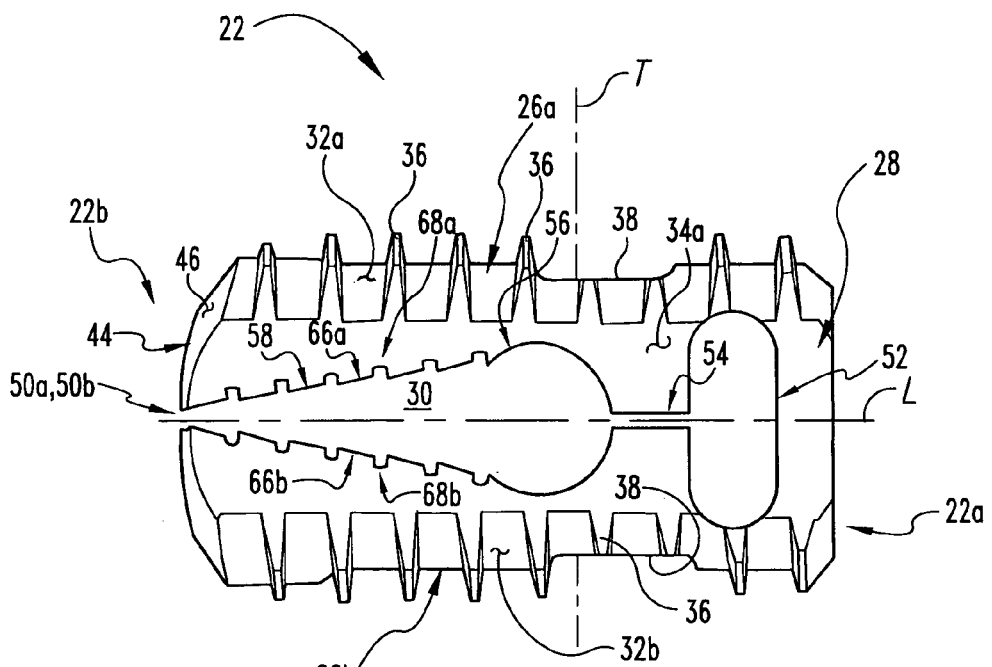
FIG. 2 is a side view of a fusion cage according to one embodiment of the present invention for use in association with the expandable fusion cage assembly illustrated in FIG. 1.
Figure 4:
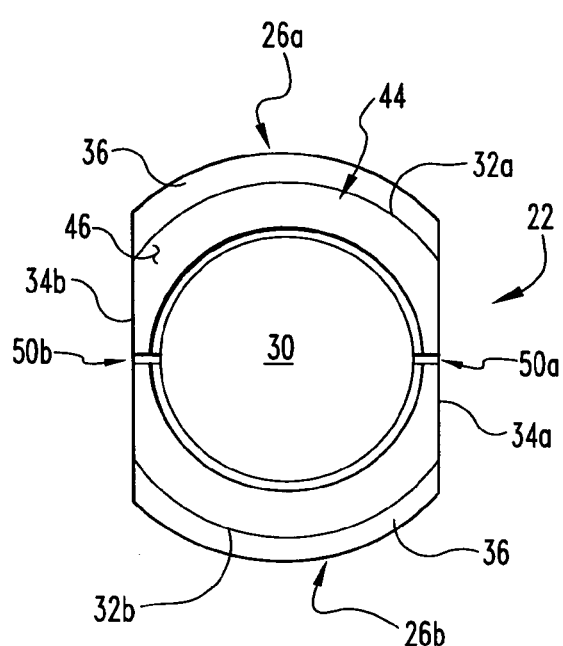
FIG. 4 is a first end view of the fusion cage illustrated in FIG. 2.
Figure 5:
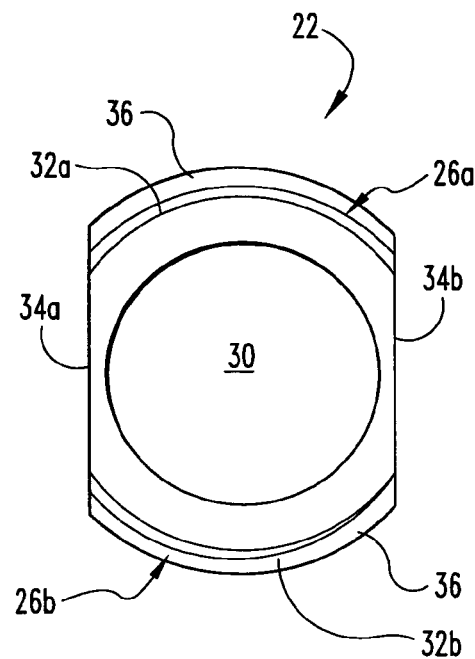
FIG. 5 is a second end view of the fusion cage illustrated in FIG. 2.

As illustrated in FIG. 3, the bone in-growth openings 40 have a slot-like configuration defining a slot length $l_S$ extending along the overall length $l_C$ of the fusion cage 22, as measured between the proximal and distal ends 22a, 22b. As also illustrated in FIG. 3, the bone in-growth openings 40 have a slot width $w_S$ extending across the overall width $w_C$ of the fusion cage 22, as measured between the outer surfaces 34a, 34b. In a specific embodiment of the invention, the slot length $l_S$ extends along at least about one half of the overall length $l_C$ of the fusion cage 22. In a further embodiment, the slot width $w_S$ extends across at least about one half of the overall width $w_C$ of the fusion cage 22. It should be understood, however, that other shapes, configurations and sizes of the bone in-growth openings 40 are also contemplated as falling within the scope of the present invention.

In a further embodiment of the invention, a bone growth promoting material 42 (FIG. 10) may be positioned within the hollow cage interior 30 to facilitate or promote bone growth through the openings 40 and into and potentially through the fusion cage 22. In one embodiment, the bone growth promoting material 42 is loaded into the hollow interior 30 subsequent to insertion of the fusion cage 22 into the intervertebral disc space D. However, it should be understood that the bone growth promoting material 42 may alternatively be positioned within the hollow interior 30 prior to insertion of the fusion cage 22 into the intervertebral disc space D. In another embodiment, the bone growth promoting material 42 is loaded into the hollow interior 30 via the opening 30a adjacent the proximal end 22a of the fusion cage 22. However, it should be understood that the bone growth promoting material 42 may alternatively be loaded into the hollow interior 30 via the opening 30b adjacent the distal end 22b, or through other openings in the fusion cage 22, such as, for example, through openings extending through the flat outer surfaces 34a, 34b or through the bone in-growth openings 40 extending through the curved outer surfaces 32a, 32b.

In one embodiment, the bone growth promoting material 42 is comprised of a bone morphogenic protein (BMP). However, other types of bone growth promoting materials are also contemplated for use in association with the present invention, such as, for example, a bone graft material including autograft bone, bone chips or bone marrow, a demineralized bone matrix (DBM), mesenchymal stem cells, a LIM mineralization protein (LMP), or any other suitable bone growth promoting material or substance that would occur to one of skill in the art. Additionally, it should be understood that the bone growth promoting material 42 may be used with or without a suitable carrier.

In another embodiment of the invention, the distal end portion 22b of the fusion cage 22, and more specifically the distal end portions of the branches 26a, 26b, cooperate to define a rounded or bullet-shaped leading end portion 44 defining a curved outer surface 46 configured to facilitate insertion of the fusion cage 22 into the intervertebral disc space D between adjacent vertebral bodies $V_U$, $V_L$ and/or to facilitate distraction of the adjacent vertebral bodies $V_U$, $V_L$. The bullet-shaped end portion 44 may be particularly useful to facilitate insertion of the fusion cage 22 into the intervertebral disc space D via an impaction or push-in technique. However, the bullet-shaped end portion 44 may also be useful to facilitate insertion and advancement of the fusion cage 22 between the adjacent vertebral bodies $V_U$, $V_L$ via other types of insertion techniques, such as, for example, a threading technique. It should be understood that the distal end portion 22b of the fusion cage 22 may take on other configurations to facilitate insertion between the adjacent vertebral bodies $V_U$, $V_L$, such as, for example, a conical, tapered or beveled configuration. It should also be understood that in other embodiments of the invention, the distal end 22b of the fusion cage 22 may define a flat or blunt configuration.

In order to facilitate expansion of the fusion cage 22, the branches 26a, 26b are separated from one another by a channel or slot extending longitudinally from the distal end 22b of the fusion cage 22 toward the proximal end 22a and terminating adjacent the fixed base portion 28. Specifically, in the illustrated embodiment, the fusion cage 22 defines a pair of channels or slots 50a and 50b extending along the flat outer surfaces 34a and 34b, respectively, and communicating with the hollow cage interior 30. Additionally, the channels 50a, 50b are positioned substantially opposite one another so as to define substantially symmetrical branch portions 26a, 26b. However, it should be understood that the channels 50a, 50b may extend along other portions of the fusion cage 22 and may be alternatively positioned so as to define non-symmetrical branch portions 26a, 26b.

In the illustrated embodiment of the invention, the channels 50a, 50b each include a first enlarged portion 52 positioned adjacent the fixed base portion 28, a relatively narrow slit portion 54 extending distally from the first enlarged portion 52 toward a second enlarged portion 56, and an inwardly tapering portion 58 extending distally from the second enlarged portion 56 toward the distal end 22b. Although a specific configuration of the channels 50a, 50b has been illustrated and described herein, it should be understood that other suitable channel or slot configurations are also contemplated as falling within the scope of the present invention.

In one embodiment of the invention, the first enlarged portion 52 has a slot-like configuration defining a slot length extending generally along the transverse axis T. The enlarged slot portion 52 tends to increase flexibility at the interconnection location between the branch portions 26a, 26b and the fixed base portion 28 so as to facilitate transitioning of the fusion cage 22 to an expanded configuration, while at the same time tending to decrease stress concentrations which might otherwise develop at the interconnection location. The enlarged slot portion 52 may also be used as a means for receiving a corresponding portion of an instrument or tool to aid in the manipulation and handing of the spinal implant assembly 20. In one embodiment of the invention, the second enlarged portion 56 has a generally circular configuration sized to receive the expansion member 24 therethrough to allow for lateral insertion of the expansion member 24 into the hollow interior 30 of the fusion cage 22. The narrow slit portion 54 extending between the first and second enlarged portions 52, 56 reduces the amount of material removed from the side walls of the branch portions 26a, 26b, thereby enclosing a greater portion of the hollow interior 30 to more fully contain the bone growth promoting material 42 within the fusion cage 22.

As illustrated in FIG. 6, the inwardly tapering portion 58 of each channel 50a, 50b is defined by opposing tapered surfaces 60a, 60b, which are in turn defined by opposing longitudinal edges of the branch portions 26a, 26b. Additionally, in the illustrated embodiment of the invention, the opposing tapered surfaces 60a, 60b are defined by a plurality of opposing pairs of discrete tapered surfaces 62a, 62b. In one embodiment, the discrete tapered surfaces 62a collectively forming the tapered surface 60a are all sloped in the same direction, and the discrete tapered surfaces 62b forming the tapered surface 60b are likewise all sloped in the same direction. However, axially adjacent ones of the discrete tapered surfaces 62a are not co-planar, but are instead transversely offset from one another so as to define a transverse shoulder 64a therebetween. Similarly, axially adjacent ones of the discrete tapered surfaces 62b are transversely offset from one another so as to define a transverse shoulder 64b therebetween, with the transverse shoulders 64a, 64b arranged in pairs and positioned generally transversely opposite one another. In this manner, the opposing pairs of tapered surfaces 62a, 62b and the oppositely disposed pairs of transverse shoulders 64a, 64b define a number of opposing pairs of ratchets 66a, 66b positioned along the length of the tapering portion 58 of each channel 50a, 50b.

As will be discussed below, the opposing ratchets 66a, 66b serve as retention elements or interlock features that engage a corresponding portion of the expansion member 24 to retain or lock the expansion member 24 in select axial positions relative to the fusion cage 22. As should be appreciated, engagement between the expansion member 24 and the opposing ratchets 66a, 66b prevents movement of the expansion member 24 in a direction opposite the transverse shoulders 64a, 64b to thereby maintain the fusion cage 22 in an expanded configuration. Additionally, in the illustrated embodiment of the invention, an opposing pair of grooves or notches 68a, 68b are defined adjacent a corresponding pair of the transverse shoulders 64a, 64b to further facilitate the retention or locking of the expansion member 24 in select axial positions relative to the fusion cage 22.

Although a specific embodiment of the retention elements or interlock features has been illustrated and described herein, it should be understood that other types and configurations of retention elements or interlock features suitable for retaining or locking the expansion member 24 in select axial positions relative to the fusion cage 22 are also contemplated. For example, embodiments using the ratchets 66a, 66b without the notches 68a, 68b, and embodiments using the notches 68a, 68b without the ratchets 66a, 66b, are also contemplated. Additionally, in another embodiment, the branch portions 26a, 26b may define internal threads adapted to threadingly engage a correspondingly threaded portion of the expansion member 24. In a further embodiment, the branch portions 26a, 26b may define a number of surface projections configured to engage a corresponding portion of the expansion member 24. In another embodiment, a retention element of interlock feature may be provided that does not require direct engagement between the fusion cage 22 and the expansion member 24. It should also be understood that ratchets 66a, 66b and/or notches 68a, 68b need not necessarily be defined along each of the tapered surfaces 60a, 60b, but may alternatively be defined along either of the tapered surfaces 60a, 60b. It should further be understood that in other embodiments of the invention, the opposing tapered surfaces 60a, 60b need not include retention elements or interlock features, but may alternatively have a substantially planar or uninterrupted configuration.

Figure 7:
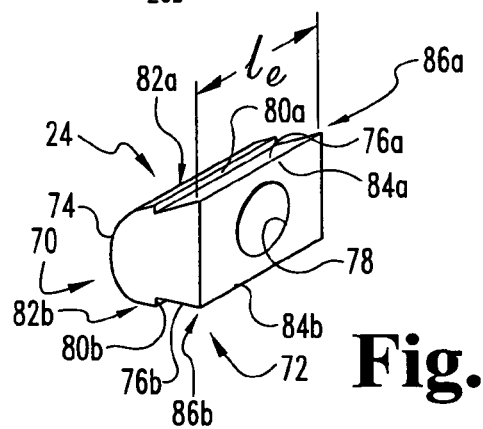
FIG. 7 is a side perspective view of an expansion member according to one embodiment of the present invention for use in association with the expandable fusion cage assembly illustrated in FIG. 1.

Referring to FIG. 7, in the illustrated embodiment of the invention, the expansion member 24 has a wedge-like configuration including a leading portion 70 and a trailing portion 72. Additionally, the expansion member 24 has a length le that is approximately equal to the overall width $w_C$ of the fusion cage 22 (FIG. 3). In this manner, the expansion member 24 is sized to engage each of the longitudinal edges, and more specifically the opposing tapered surfaces 60a, 60b of the branch portions 26a, 26b. As will be discussed below, axial advancement of the expansion member 24 along the hollow interior 30 of the fusion cage 22, and more specifically along the opposing tapered surfaces 60a, 60b, results in transitioning of the fusion cage 22 to an expanded configuration.

In the illustrated embodiment of the expansion member 24, the leading portion 70 includes a curved or tapered surface 74 to facilitate sliding advancement of the expansion member 24 along the opposing tapered surfaces 60a, 60b of the branch portions 26a, 26b. However, it should be understood that other configurations of the leading portion 70 are also contemplated. The trailing portion 72 of the expansion member 24 preferably includes a pair of opposite tapered surface 76a, 76b that are angled to substantially correspond to the taper angle of the opposing tapered surfaces 60a, 60b of the branch portions 26a, 26. The trailing portion 72 also includes a central opening 78 adapted to engagingly receive a distal end portion of a driving tool therein to aid in axially displacing the expansion member 24 through the fusion cage 22. The opening 78 may be threaded so as to threadingly engage a distal end portion of a driving tool therein to provide for more secure engagement between the tool and the expansion member 24.

As shown in FIG. 10, the trailing portion 72, and more specifically the tapered surfaces 76a, 76b, bear against the opposing tapered surfaces 60a, 60b of the branch portions 26a, 26b when the fusion cage 22 is transitioned to a partially expanded or fully expanded configuration. Engagement between the tapered surfaces 76a, 76b of the expansion member 24 and the opposing tapered surfaces 60a, 60b of the branch portions 26a, 26b aids in maintaining the fusion cage 22 in a partially expanded or fully expanded configuration, and also tends to increase the stability of the fusion cage 22 when transitioned to an expanded configuration. Additionally, the tapered surfaces 76a, 76b of the trailing portion 72 are preferably inwardly offset relative to the leading portion 70 so as to define a pair of opposite transverse shoulders or ridges 80a, 80b. The transverse shoulders 80a, 80b in turn define a pair of opposite pawls 82a, 82b that are configured for engagement with a corresponding pair of opposing ratchets 66a, 66b defined along the longitudinal tapered surfaces or edges 60a, 60b of the branch portions 26a, 26b. Additionally, the trailing end surface of the expansion member 24 defines a pair of opposite corner portions or shoulders 84a, 84b which in turn define a second pair of opposite pawls 86a, 86b that are configured for engagement with a corresponding pair of opposing ratchets 66a, 66b.

Although a specific embodiment of the expansion member 24 is illustrated and described herein, it should be understood that other suitable configurations of the expansion member 24 are also contemplated as falling within the scope of the present invention. For example, the expansion member 24 may be provided with other elements or features that engage or otherwise cooperate with the branch portions 26a, 26b so as to retain or lock the expansion member 24 in select axial positions relative to the fusion cage 22. For example, as indicated above, the branch portions 26a, 26b may define internal threads that are adapted to threadingly engage a correspondingly threaded portion of the expansion member 24. Additionally, it should be understood that the pawls 82a, 82b and 86a, 86b need not necessarily extend along the entire length le of the expansion member 24, but may alternatively be defined along the lateral end portions of the expansion member 24 so as to provide engagement with the tapered longitudinal edges 60a, 60b of the branch portions 26a, 26b. It should also be understood that the expansion member 24 need not necessarily include first and second pairs of pawls 82a, 82b and 86a, 86b, but may alternatively define a single pair of pawls.

Figure 8:
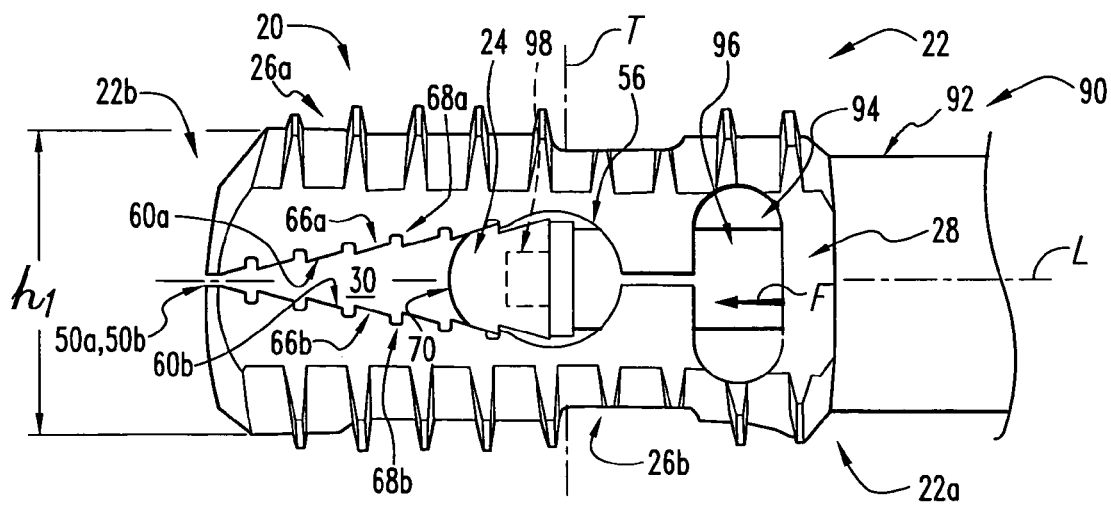
FIG. 8 is a side view of the expandable fusion cage assembly illustrated in FIG. 1, as shown in a non-expanded configuration with the expansion member disposed at a first operational position within the fusion cage.
Figure 9:
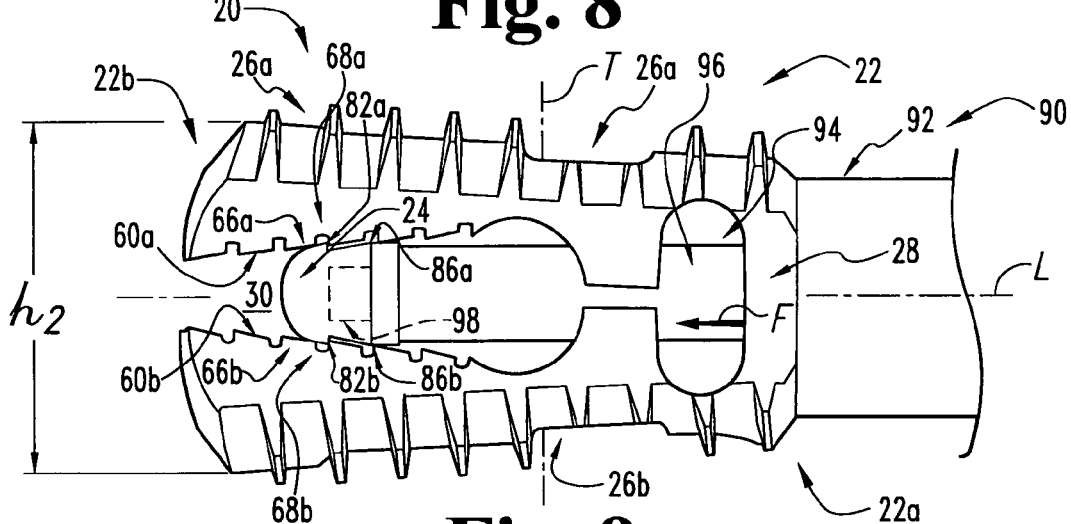
FIG. 9 is a side view of the expandable fusion cage assembly illustrated in FIG. 1, as shown in a partially-expanded configuration with the expansion member disposed at a second operational position within the fusion cage.

Referring to FIGS. 8-10, shown therein are three operational positions of the expansion member 24 relative to the fusion cage 22 according to one embodiment of the invention. FIG. 8 illustrates a first operational position wherein the expansion member 24 is positioned adjacent the enlarged circular portion 56 defined by the slots 50a, 50b extending along the branch portions 26a, 26b. In this first operational position, the fusion cage 22 is a maintained in a non-expanded configuration, with the branch portions 26a, 26b arranged substantially parallel to one another. As should be appreciated, the fusion cage 22 may be inserted into the intervertebral disc space D between the upper and lower vertebrae $V_U$, $V_L$ while in the non-expanded configuration via either a threading technique or a push-in/impaction technique.

Once inserted into the intervertebral disc space D, the fusion cage 22 may be selectively transitioned to a partially expanded configuration, as illustrated in FIG. 9, or to a fully expanded configuration, as illustrated in FIG. 10. However, it should be understood that in other embodiments of the invention, the fusion cage 22 may be selectively transitioned to a partially or fully expanded configuration prior to being inserted into the intervertebral disc space D. As should be appreciated, the degree of expansion of the fusion cage 22 corresponds to the selected operational position of the expansion member 24 along the longitudinal axis L which, as discussed above, may be selectively controlled via engagement of the pairs of pawls 82a, 82b and 86a, 86b with corresponding pairs of the opposing ratchets 66a, 66b. As will be discussed below, when the fusion cage 22 is transitioned to a partially or fully expanded configuration, the branch portions 26a, 26b are angled relative to one another so as to define an outwardly tapered configuration extending from the proximal end 22a toward the distal end 22b.

As illustrated in FIGS. 9 and 10, since the movable branch portions 26a, 26b are integrally connected with one another via the fixed base portion 28, expansion of the fusion cage 22 is not uniform along the length $l_C$ of the fusion cage 22. Instead, the fixed proximal ends of the branch portions 26a, 26b adjacent the fixed base portion 28 remain relatively stationary, and therefore do not appreciably expand along the transverse axis T. However, the movable distal ends of the branch portions 26a, 26b separate or splay apart to transversely expand the distal end portion of the fusion cage 22 from an initial height $h_1$ (FIG. 8) to expanded heights $h_2$ and $h_3$ (FIGS. 9 and 10).

As illustrated in FIGS. 8 and 9, an instrument or tool 90 may be provided to aid in the manipulation and handling of the spinal implant assembly 20 and to axially displace the expansion member 24 relative to the fusion cage 22 to facilitate transitioning of the fusion cage 22 toward an expanded configuration. In the illustrated embodiment, the instrument 90 generally comprises an outer sleeve 92 and an inner actuator shaft 94. The surgical instrument 90 may also include a handle (not shown) to further aid in the manipulation and handling of the spinal implant assembly 20.

The outer sleeve 92 is engaged with the proximal end portion 22a of the fusion cage 22. In one embodiment, engagement between the outer sleeve 92 and the fusion cage 22 is abutting engagement. However, it should be understood that other types of engagement are also contemplated, such as, for example, threaded engagement, keyed engagement, tongue-and-groove engagement, frictional engagement, or any other suitable method of engagement. The actuator shaft 94 is disposed within the outer sleeve 92 and includes a distal portion 96 extending through the proximal opening 30a and into the hollow interior 30 of the fusion cage 22, with a distal-most end portion 98 engaging the expansion member 24. In one embodiment of the invention, the distal-most end portion 98 is received within the central opening 78 in the expansion member 24. In the illustrated embodiment, the distal-most end portion 98 has a generally circular outer cross section that closely corresponds with the inner circular cross section of the opening 78 to provide secure engagement between the actuator shaft 94 and the expansion member 24. However, other shapes and configurations of the distal-most end portion 98 are also contemplated for use in association with the present invention, including rectangular or hexagonal configurations. Additionally, various types of engagement between the tool 90 and the expansion member 24 are contemplated, such as, for example, abutting engagement, threaded engagement, keyed engagement, tongue-and-groove engagement, frictional engagement, or any other suitable method of engagement.

Although a specific embodiment of the instrument 90 has been illustrated and described herein, it should be understood that other embodiments of instruments or tools suitable for use in association with the spinal implant assembly 20 are also contemplated, and that the features, elements and operation thereof may differ from those associated with the surgical instrument 90. One example of another embodiment of an instrument 200 suitable for use in association with the spinal implant assembly 20 is illustrated in FIGS. 13-16 and described below. Another example of a suitable instrument is illustrated and described in U.S. Pat. No. 6,436,140 to Liu et al., the entire contents of which are hereby incorporated herein by reference.

As should be appreciated, application of an axial force F onto the actuator shaft 94 correspondingly displaces the expansion member 24 relative to the fusion cage 22 generally along the longitudinal axis L. As the expansion member 24 is axially displaced through the fusion cage 22, the branch portions 26a, 26b are separated or splayed apart to transition the fusion cage 22 toward a partially expanded configuration (FIG. 9) or to a fully expanded configuration (FIG. 10). More specifically, as the leading portion 70 of the expansion member 24 is slidably engaged along the inwardly tapering surfaces 60a, 60b of the branch portions 26a, 26b, the expansion member 24 acts as a wedge to drive the branch portions 26a, 26b apart to thereby expand the fusion cage 22 along the transverse axis T.

As should also be appreciated, engagement of the pairs of pawls 82a, 82b and 86a, 86b with corresponding pairs of the opposing ratchets 66a, 66b serves to retain the expansion member 24 in a select axial position relative to the fusion cage 22. Specifically, abutment of the transverse shoulders 80a, 80b of the pawls 82a, 82b and the corners or edges 84a, 84b of the pawls 86a, 86b against the transverse shoulders 64a, 64b of the corresponding ratchets 66a, 66b prevents backward movement of the expansion member 24 in a trailing direction (e.g., toward the fixed base portion 28). Additionally, a portion of the pawls 82a, 82b and 86a, 86b may be positioned within corresponding opposing pairs of the notches 68a, 68b to further aid in retaining the expansion member 24 in the select axial position relative to the fusion cage 22.

As should further be appreciated, the ratchets 66a, 66b and the pairs of pawls 82a, 82b and 86a, 86b are configured and arranged so as to allow relatively uninhibited forward movement of the expansion member 24 in a leading direction (e.g., toward the distal end 22b) to allow for transitioning of the fusion cage 22 toward an expanded configuration. However, interlocking engagement between the ratchets 66a, 66b and the pawls 82a, 82b and 86a, 86b retains the expansion member 24 in a select axial position to maintain the fusion cage 22 in a partially expanded or fully expanded configuration. Additionally, since the branch portions 26a, 26b define a series of opposing pairs of ratchets 66a, 66b disposed at various axial locations along the tapered surfaces 60a, 60b, the fusion cage 22 may be selectively transitioned to predetermined states or degrees of expansion.

Selective transitioning of the fusion cage 22 to predetermined states or degrees of expansion may thereby serve to more closely match the structural configuration and shape of the fusion cage 22 to the patient's spinal anatomy. For example, controlling expansion of the fusion cage 22 also controls the taper angle between the branch portions 26a, 26b so as to more closely match the lordotic angle between the upper and lower vertebrae $V_U$, $V_L$. If the fusion cage 22 is inserted into the intervertebral disc space prior to transitioning to an expanded configuration, expansion of the fusion cage 22 may also serve to distract the intervertebral disc space in addition to restoring and/or maintaining lordosis between the upper and lower vertebrae $V_U$, $V_L$. Following expansion of the fusion cage 22, the surgical instrument 90 may be disengaged from the spinal implant assembly 20 and removed from the patient. As discussed above, a bone growth promoting material 42 (FIG. 10) may be loaded into the hollow interior 30 of the fusion cage 22 to facilitate or promote bone growth from the upper and lower vertebrae $V_U$, $V_L$, through the bone in-growth openings 40 and into and possibly through the fusion cage 22.

Having illustrated and described the elements and operation of the spinal implant assembly 20, reference will now be made to a technique for implanting the spinal implant assembly 20 within an intervertebral disc space according to one embodiment of the invention. However, it should be understood that other implantation techniques and procedures are also contemplated, and that the following technique in no way limits the scope of the present invention.

Referring to FIGS. 11 and 12, the vertebral level to be treated is initially identified, followed by the removal of at least a portion of the natural intervertebral disc via a total or partial discectomy. The endplates of the upper and lower vertebrae $V_U$, $V_L$ may then be prepared using known surgical instruments and techniques (e.g., rotating cutters, curettes, chisels, etc.). In one embodiment, a tapping instrument may be used to cut threads along the endplates of the upper and lower vertebrae $V_U$, $V_L$ to allow the fusion cage 22 to be threadingly inserted into the intervertebral disc space D. However, in another embodiment of the invention, the threads 36 formed along the fusion cage 22 may be self-tapping threads so as to eliminate the need to pre-cut threads along the vertebral endplates.

Following preparation of the intervertebral disc space D and the upper and lower vertebrae $V_U$, $V_L$, the spinal implant assembly 20 is inserted into the intervertebral disc space D via a suitable insertion technique, such as, for example, via a threading technique or by an impaction/push-in type technique. The bullet-shaped leading end portion 44 of the fusion cage 22 facilitates insertion between the upper and lower vertebrae $V_U$, $V_L$. As discussed above, in one embodiment of the invention, the spinal implant assembly 20 may be inserted into the intervertebral disc space D while the fusion cage 22 in a non-expanded configuration (FIG. 8). However, in some instances it may be desirable to transition the spinal implant assembly 20 to a partially expanded or fully expanded configuration (FIGS. 9 and 10) either before or during insertion into the intervertebral disc space D.

Insertion of the spinal implant assembly 20 into the intervertebral disc space D while in a non-expanded configuration is particularly applicable when the fusion cage 22 is inserted via a threading technique so as to minimize neural distraction. In the non-expanded configuration, the branch portions 26a, 26b are arranged substantially parallel to one another to provide the fusion cage 22 with a substantially uniform outer dimension between the threaded arcuate surfaces 32a, 32b along substantially the entire length of the fusion cage 22. In a further embodiment of the invention, the spinal implant assembly 20 may be inserted into the intervertebral disc space D in a minimally invasive manner (i.e., through a small access portal) via the use of endoscopic equipment, a small diameter tube or cannula, or by other suitable minimally invasive surgical techniques. Minimally invasive insertion of the spinal implant assembly 20 into the disc space D is preferably accomplished with the assembly 20 maintained in a non-expanded configuration.

As illustrated in FIGS. 11 and 12, the fusion cage 22 has a height dimension $h_C$ measured between the threaded outer surfaces 32a, 32b and a width dimension $w_C$ measured between the truncated outer surfaces 34a, 34b which is less than the height dimension $h_C$. This truncated configuration of the fusion cage 22 allows for insertion into the intervertebral disc space D with the truncated outer surfaces 34a, 34b arranged generally parallel to the vertebral endplates of the upper and lower vertebrae $V_U$, $V_L$, and with the width dimension $w_C$ aligned generally along the axis A of the vertebral column (FIG. 11). The fusion cage 22 may then be rotated ninety (90) degrees in the direction of arrow R to engage the threaded outer surfaces 32a, 32b with the upper and lower vertebral endplates, with the height dimension $h_C$ aligned generally along the axis A of the vertebral column (FIG. 12). Engagement of the threads 36 with the upper and lower vertebral endplates inhibits movement of the fusion cage 22 relative to the upper and lower vertebrae $V_U$, $V_L$, and also reduces the risk of expulsion of the fusion cage 22 from the intervertebral disc space D.

As should be appreciated, the above-described technique for inserting the spinal implant assembly 20 into the intervertebral disc space D minimizes distraction of the upper and lower vertebrae $V_U$, $V_L$ which likewise reduces neural distraction. As should also be appreciated, this technique may be particularly beneficial in instances where the fusion cage 22 is transitioned to an expanded configuration prior to being inserted into the disc space D. Additionally, removal or revision of the fusion cage 22 can be easily accomplished by simply rotating the fusion cage 22 ninety (90) degrees to disengage the threaded surfaces 32a, 32b from the upper and lower vertebrae $V_U$, $V_L$ to once again arrange the truncated outer surfaces 34a, 34b parallel to the vertebral endplates of the upper and lower vertebrae $V_U$, $V_L$. At this point, the fusion cage 22 can be easily removed from and/or repositioned within the intervertebral disc space D without necessarily having to transition the fusion cage 22 back to the initial non-expanded configuration (FIG. 8).

Once the spinal implant assembly 20 is inserted into the intervertebral disc space D and arranged in the orientation illustrated in FIG. 12, the fusion cage 22 is then transitioned to a partially expanded or fully expanded configuration (FIGS. 9 and 10). However, as discussed above, in other embodiments of the invention, the fusion cage 22 may be transitioned to a partially expanded or fully expanded configuration prior to insertion into the intervertebral disc space D. As also discussed above, the fusion cage 22 may be transitioned to an expanded configuration via axial displacement of the expansion member 24 along the tapered surfaces 60a, 60b, which in turn causes the branch portions 26a, 26b to separate or splay apart to distract and/or restore/maintain lordosis between the upper and lower vertebrae $V_U$, $V_L$. Moreover, the degree of expansion of the fusion cage 22 and the taper angle defined between the branch portions 26a, 26b corresponds to the axial position of the expansion member 24 which, as discussed above, may be selectively controlled via engagement of the pawls 82a, 82b and 86a, 86b with corresponding pairs of the opposing ratchets 66a, 66b. Accordingly, the degree of expansion and the taper angle may be selected/adjusted in situ to tailor the configuration of the fusion cage 22 to the specific spinal anatomy of the patient being treated.

Following expansion of the fusion cage 22, a bone growth promoting material 42 (FIG. 10) may be injected or otherwise loaded into the hollow interior 30 of the fusion cage 22 to facilitate or promote bone growth from the upper and lower vertebrae $V_U$, $V_L$, through the bone growth openings 40, and into and possibly through the fusion cage 22. However, as indicated above, the bone growth promoting material 42 may be positioned within the hollow interior 30 prior to or during insertion and/or expansion of the fusion cage 22. A morselized autograft bone or a similar type of material may also be positioned adjacent the expanded fusion cage 22 to further promote bony fusion. Additionally, in some instances it may be desirable to remove a portion of the upper and lower vertebral endplates to expose cancellous bone into direct contact with the fusion cage 22 and/or with the bone growth promoting material 42 disposed therein to further facilitate bony ingrowth and fusion between the fusion cage 22 and the upper and lower vertebrae $V_U$, $V_L$.

In one embodiment of the invention, access to the spinal column and insertion of the spinal implant assembly 20 into the intervertebral disc space D is accomplished via a posterior surgical approach. However, it should be understood that access to and insertion of the spinal implant assembly 20 into the intervertebral disc space D may be accomplished via other surgical approaches, such as, for example, an anterior approach or a lateral approach. In another embodiment of the invention, the spinal implant assembly 20 is used to treat the lumbar region of the spine, with the upper and lower vertebrae $V_U$, $V_L$ comprising lumbar vertebrae. However, it should nevertheless be understood that the present invention is also applicable to other portions of the spine, including the cervical, thoracic or sacral regions of the spine. Additionally, in a further embodiment of the invention, a pair of the spinal implant assemblies 20 may be positioned side-by-side in a bilateral arrangement within the intervertebral disc space D. However, it should be understood that unilateral placement or central placement of a single spinal implant assembly 20 within the intervertebral disc space D is also contemplated as falling within the scope of the present invention.

Referring to FIGS. 13-16, shown therein is an instrument or tool 200 according to another form of the present invention for use in association with a spinal implant assembly 300. The spinal implant assembly 300 is configured similar to the spinal implant assembly 20 illustrated and described above, generally comprising an expandable fusion cage 322 and an expansion member 324. In the illustrated embodiment, the fusion cage 322 includes a pair of movable branch portions 326a, 326b flexibly interconnected to one another via a fixed base portion 328 such that axial displacement of the expansion member 324 between the branch portions 326a, 326b causes the branch portions 326a, 326b to separate or splay apart. Additionally, the branch portions 326a, 326b cooperate with one another to define a substantially hollow cage interior 330 which preferably extends entirely through the fusion cage 322 so as to define an open proximal end and an open distal end. The fusion cage 322 includes a pair of arcuate outer surfaces 332a and 332b formed along the branch portions 326a, 326b, each defining external threads 336. A bone ingrowth opening 340 extends through each of the arcuate outer surfaces 332a, 332b in communication with the hollow cage interior 330. The branches 326a, 326b are separated from one another by a channel defining opposing tapered surfaces 360a, 360b, which in turn define a number of opposing pairs of ratchets 366a, 366b. The pairs of ratchets 366a, 366b cooperate with opposite pawls 382a, 382b and 386a, 386b defined by the expansion member 324 to retain or lock the expansion member 324 in a select axial position relative to the fusion cage 322.

The instrument 200 is adapted to selectively engage the spinal implant assembly 300 to aid in the manipulation and handling thereof and to axially displace the expansion member 324 relative to the fusion cage 322 to facilitate transitioning of the fusion cage 322 toward an expanded configuration. In the illustrated embodiment, the instrument 200 extends along a longitudinal axis L and is generally comprised of an outer sleeve member 202, an inner actuator member 204, a handle member 206 disposed adjacent a proximal end portion 200a of the instrument, and an engagement mechanism 208 disposed adjacent a distal end portion 200b of the instrument.

In the illustrated embodiment of the instrument 200, the sleeve member 202 includes an axial passage 210 extending therethrough, and the actuator member 204 includes a shaft portion 212 and a proximal portion 214. The shaft portion 212 is sized and shaped to extend through the axial passage 210 in the sleeve member 202. In one embodiment, the axial passage 210 and the shaft portion 212 each have a generally circular configuration; however, other suitable shapes and configurations are also contemplated. The proximal portion 214 of the actuator member 204 defines external threads 216 and a tool receiving opening 218. The handle member 206 is engaged with a proximal end portion of the outer sleeve 202 and defines an internally threaded axial passage 220 adapted to threadingly receive the threaded proximal portion 214 of the actuator member 204 therein.

In the illustrated embodiment, the handle member 206 comprises an outer gripping portion 222 and an insert portion 224. The gripping portion 222 defines an axial passageway 226 sized and shaped to receive the insert portion 224 therein. The insert portion 224 defines the threaded axial passage 220 and includes a knob portion 228 extending from the proximal end of the gripping portion 222. The insert portion 224 is rotatable within the axial passageway 226 via application of a rotational force onto the knob portion 228, which in turn results in threading engagement of the threaded proximal portion 214 of the actuator member 204 along the threaded axial passage 220 to correspondingly displace the actuator shaft portion 212 along the longitudinal axis L. However, in another embodiment of the invention, the handle member 206 may be configured as a single piece structure (e.g., with no separate insert portion 226). In this manner, application of a rotational force onto a driver instrument (not shown) having a shaped distal end portion positioned within the tool receiving opening 218 in the threaded proximal portion 214 of the actuator member 204 drives the threaded proximal portion 214 along the axial threaded passage 220 to correspondingly displace the actuator shaft 212 along the longitudinal axis L.

In the illustrated embodiment of the instrument 200, the engagement mechanism 208 is adapted to selectively engage and disengage the spinal implant assembly 300. In one embodiment of the invention, the engagement mechanism 208 comprises a pair of oppositely disposed engagement arms 230a, 230b. In another embodiment, the engagement arms 230a, 230b are pivotally coupled to a distal portion of the sleeve member 202 in such a manner as to allow pivotal movement of the engagement arms 230a, 230b between a retracted/disengaged configuration (FIG. 14) and an expanded/engaged configuration (FIG. 15), the details of which will be discussed below. In a further embodiment, the engagement arms 230a, 230b are pivotally coupled to the sleeve member 202 to allow pivotal movement about pivot axes $P_1$ and $P_2$, respectively, with the pivot axes $P_1$, $P_2$ being offset and arranged substantially parallel to one another.

In the illustrated embodiment of the invention, the engagement arms 230a, 230b include axial portions 232a, 232b and transverse flange portions or bosses 234a, 234b. The axial portions 232a, 232b are at least partially disposed within and extend generally along the axial passage 210 in the sleeve member 202 and are pivotally coupled to the sleeve member 202 via a hinge pins 236a, 236b. The transverse flange portions 234a, 234b are positioned outside the axial passage 210 adjacent the distal end of the sleeve member 202 and extend in generally opposite transverse directions. In one embodiment of the invention, the engagement arms 230a, 230b are biased such that the transverse flange portions 234a, 234b are urged toward one another in such a manner as to provide the retracted configuration illustrated in FIG. 14. Biasing of the engagement arms 230a, 230b toward the retracted configuration can be provided via a number of methods. For example, in one embodiment, one or more springs (not shown) engaged between the sleeve member 202 and the engagement arms 230a, 230b can be used to bias the engagement arms 230a, 230b toward the retracted configuration. However, other configurations and embodiments for biasing the engagement arms 230a, 230b toward the retracted configuration are also contemplated.

Figure 13:
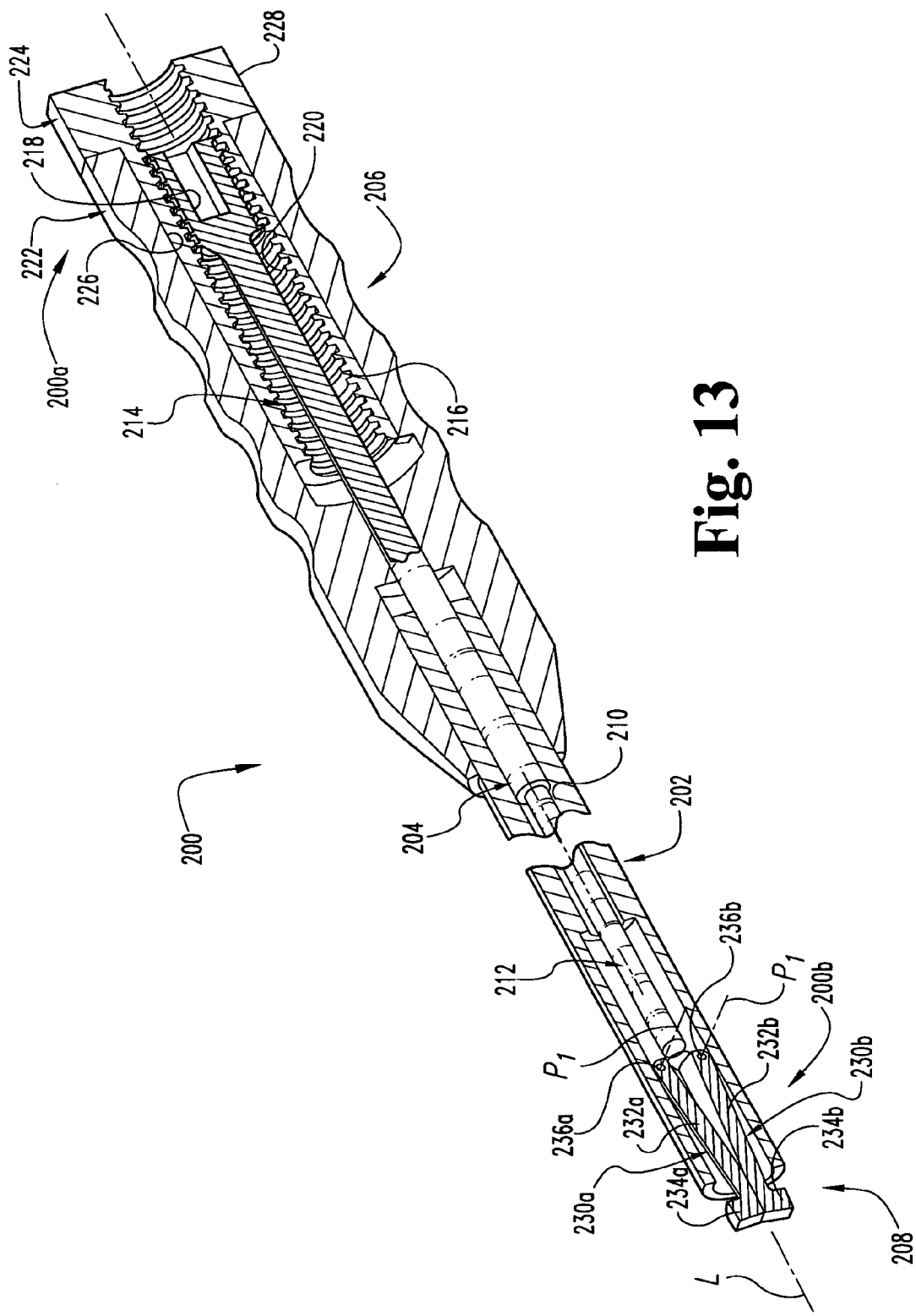
FIG. 13 is a cut-away side perspective view, partially in cross section, of an instrument according to one form of the present invention for inserting a fusion cage assembly into an intervertebral disc space and for transitioning the fusion cage assembly toward an expanded configuration.
Figure 14:
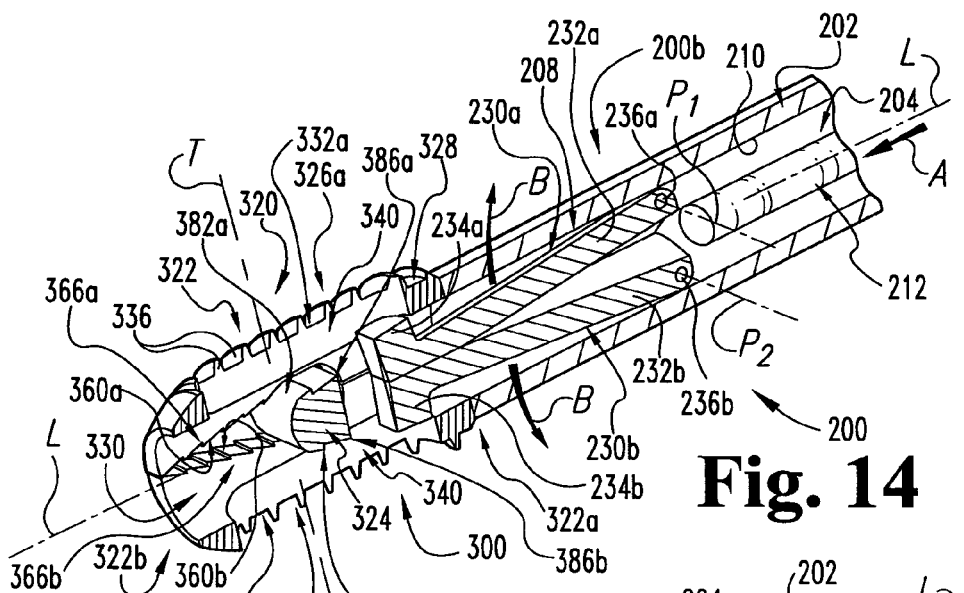
FIG. 14 is a cut-away side perspective view, partially in cross section, of the distal end portion of the instrument illustrated in FIG. 13, as positioned adjacent the proximal end portion of a fusion cage assembly.

Referring to FIG. 14, the instrument 200 is shown in a retracted configuration wherein the engagement arms 230a, 230b are inwardly biased toward one another such that the transverse flange portions 234a, 234b are positioned adjacent one another to define a reduced transverse profile. The retracted transverse flange portions 234a, 234b are inserted through the open proximal end of the fusion cage 300 and into the hollow cage interior 330, with the distal end of the sleeve member 202 positioned adjacent the proximal end of the fusion cage 300 and with the transverse flange portions 234a, 234b positioned adjacent the bone in-growth openings 340. The shaft portion 212 of the actuator member 204 is then axially advanced through the outer sleeve 202 in the direction of arrow A via application of a rotational force onto the knob portion 228 of the handle member 206 (FIG. 13). As should be appreciated, axial advancement of the shaft portion 212 in turn displaces the distal end of the shaft 212 between the engagement arms 230a, 230b which results in outward pivotal movement of the engagement arms 230a, 230b in the direction of arrows B.

Figure 15:
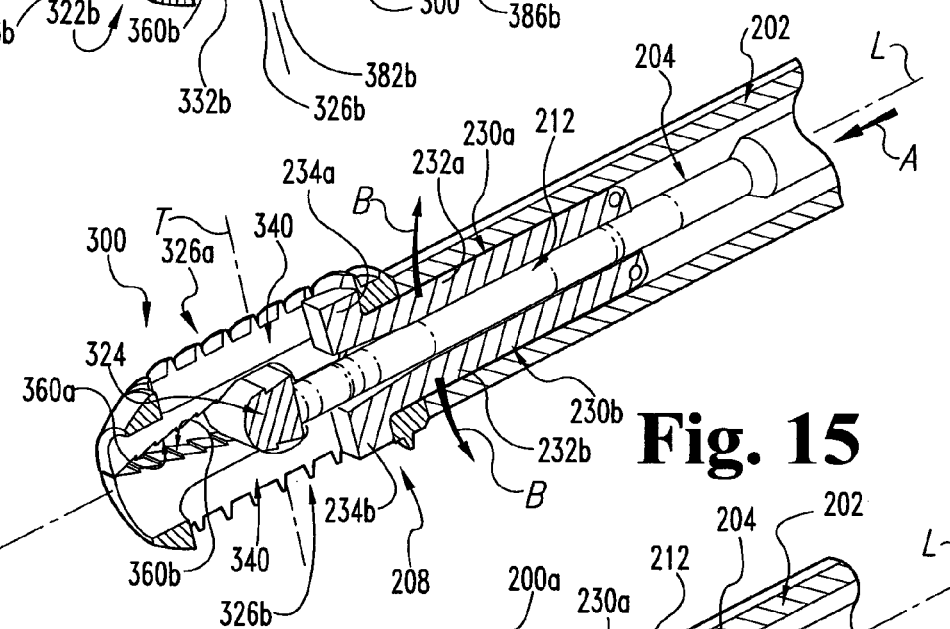
FIG. 15 is a cut-away side perspective view, partially in cross section, of the distal end portion of the instrument illustrated in FIG. 13, as engaged to the proximal end portion of the fusion cage assembly and as engaged to the expansion member for displacing the expansion member in an axial direction to transition the fusion cage assembly toward an expanded configuration.

Referring to FIG. 15, continued axial advancement of the shaft portion 212 in the direction of arrow A transitions the engagement arms 230a, 230b to an expanded/engaged configuration. Specifically, axial advancement of the shaft portion 212 between the engagement arms 230a, 230b outwardly pivots the engagement arms 230a, 230b away from one another in the direction of arrows B which in turn outwardly displaces the transverse flange portions 234a, 234b into engagement within the bone in-growth openings 340 in the fusion cage 300 to selectively and securely engage the instrument 200 with the fusion cage 300. However, it should be understood that the transverse flange portions 234a, 234b need not necessarily be positioned within the bone in-growth openings 340 to provide selective and secure engagement between the instrument 200 and the fusion cage 300, but may instead be positioned within other apertures or openings defined by the fusion cage 300 and/or engaged with other portions of the fusion cage 300.

Figure 16:
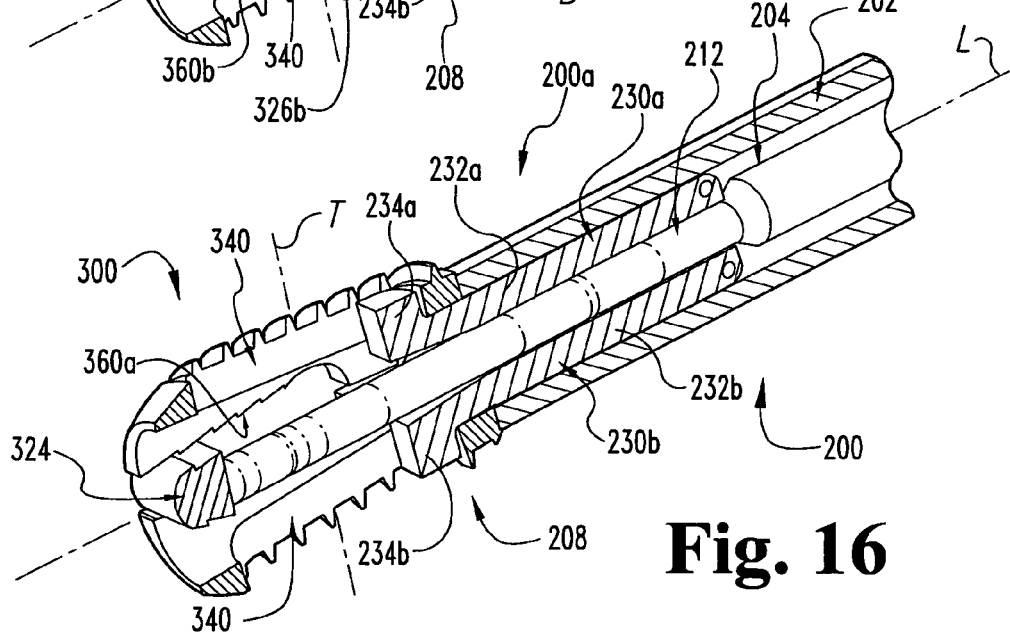
FIG. 16 is a side perspective view, partially in cross section, of the distal end portion of the instrument illustrated in FIG. 13, as shown in a fully extended position to transition the fusion cage assembly to a fully expanded configuration.

Referring to FIG. 16, continued axial advancement of the shaft portion 212 in the direction of arrow A results in engagement of the distal end of the shaft portion 212 against the expansion member 324, which correspondingly axially advances the expansion member 324 along the hollow interior 330 to transition the fusion cage 300 to an expanded configuration. Specifically, as the expansion member 324 is axially displaced through the hollow interior 330, the branch portions 326a, 326b are separated or splayed apart via sliding engagement between the expansion member 324 and the opposing tapered surfaces 360a, 360b, thereby resulting in expansion of the fusion cage 322 generally along the transverse axis T. As discussed above with regard to the fusion cage 22, the opposite pawls 382a, 382b and 386a, 386b defined by the expansion member 324 engage corresponding pairs of the opposing ratchets 366a, 366b to retain or lock the expansion member 324 in a select axial position relative to the fusion cage 322, thereby maintaining the fusion cage 322 in a partially or fully expanded configuration.

Once the fusion cage 322 is transitioned to an expanded configuration, the shaft portion 212 of the actuator member 204 is retracted from fusion cage 322 via application of a rotational forces onto the knob portion 228 of the handle member 206 (FIG. 13). As should be appreciated, since the engagement arms 230a, 230b are inwardly biased toward one another, removal of the shaft portion 212 from between the engagement arms 230a, 230b results in inward pivotal back toward the retracted configuration illustrated in FIG. 14. Inward pivotal movement of the engagement arms 230a, 230b in turn inwardly displaces the transverse flange portions 234a, 234b and disengages the flange portions 234a, 234b from the bone in-growth openings 340, thereby allowing for selective disengagement of the instrument 200 from the fusion cage 300 and removal of the instrument 200 from the surgical site.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An expandable spinal implant, comprising:
a cage body extending along a longitudinal axis and including at least two movable branches having first end portions that are interconnected to one another and opposite second end portions that are movable relative to one another, said movable branches cooperating to define a hollow interior of said cage body and including:
a first shell portion having a substantially semi-cylindrical shape and including a first pair of longitudinal edges and defining a first hollow region between said first pair of longitudinal edges, each of said first pair of longitudinal edges extending from an outer surface of said cage body to said first hollow region;
a second shell portion having a substantially semi-cylindrical shape and including a second pair of longitudinal edges and defining a second hollow region between said second pair of longitudinal edges, each of said second pair of longitudinal edges extending from said outer surface of said cage body to said second hollow region;
wherein said first and second shell portions cooperate with one another to provide said cage body with a substantially cylindrical configuration with said first hollow region of said first shell portion cooperating with said second hollow region of said second shell portion to define at least a portion of said hollow interior of said cage body, and with said first pair of longitudinal edges arranged generally opposite said second pair of longitudinal edges to define opposing pairs of inwardly tapered longitudinal edges extending along said longitudinal axis; and
wherein said cage body defines external threads configured for engagement with adjacent vertebral bodies; and
an expansion member slidably engaged simultaneously along said opposing pairs of inwardly tapered longitudinal edges as said expansion member is axially displaced along said longitudinal axis between said first and second shell portions to transition said cage body toward a transversely expanded configuration.

2. The implant of claim 1, wherein said first and second pairs of longitudinal edges are arranged transversely opposite one another and are substantially planar.

3. The implant of claim 1, wherein said cage body has a generally circular outer cross section having truncated side portions arranged generally opposite one another and interrupting said external threads.

4. The implant of claim 1, wherein at least one of said longitudinal edges of said first and second shell portions defines a plurality of retention elements positioned at select axial locations, said expansion member engaged with at least one of said retention elements to retain said expansion member at a select axial position between said first and second shell portions and to maintain said cage body in said transversely expanded configuration.

5. The implant of claim 4, wherein said retention elements comprise ratchets.

6. The implant of claim 4, wherein each of said first and second pairs of longitudinal edges of said first and second shell portions defines a plurality of retention elements positioned at select axial locations, said expansion member engaged with at least one of said retention elements defined by each of said longitudinal surfaces to retain said expansion member at a select axial location between said first and second shell portions and to maintain said cage body in said transversely expanded configuration.

7. The implant of claim 1, wherein said second end portions of said movable branches are configured to provide said cage body with a rounded leading end portion to facilitate insertion of said cage body between adjacent vertebral bodies.

8. The implant of claim 7, wherein said rounded leading end portion is bullet-shaped.

9. The implant of claim 1, wherein said expansion member is sized to engage each of said longitudinal edges of said first and second shell portions as said expansion member is axially displaced along said longitudinal axis to transition said cage body toward said transversely expanded configuration.

10. The implant of claim 1, wherein said expansion member has a length extending substantially entirely across an overall width of said cage body.

11. The implant of claim 1, wherein said expansion member includes a rounded leading end portion to facilitate sliding engagement between opposing ones of said first and second pairs of longitudinal surfaces to transition said cage body toward said transversely expanded configuration.

12. An expandable spinal implant, comprising:
a cage body extending along a longitudinal axis and including at least two movable branches having first end portions that are interconnected to one another and opposite second end portions that are movable relative to one another, said movable branches cooperating to define a hollow interior of said cage body and including:
a first shell portion having a substantially semi-cylindrical shape and including a first pair of longitudinal edges and defining a first hollow region between said first pair of longitudinal edges, each of said first pair of longitudinal edges extending from an outer surface of said cage body to said first hollow region;
a second shell portion having a substantially semi-cylindrical shape and including a second pair of longitudinal edges and defining a second hollow region between said second pair of longitudinal edges, each of said second pair of longitudinal edges extending from said outer surface of said cage body to said second hollow region;
wherein said first and second shell portions cooperate with one another to provide said cage body with a substantially cylindrical configuration with said first hollow region of said first shell portion cooperating with said second hollow region of said second shell portion to define at least a portion of said hollow interior of said cage body, and with said first pair of longitudinal edges arranged generally opposite said second pair of longitudinal edges to define opposing pairs of inwardly tapered longitudinal edges extending along said longitudinal axis; and
wherein said cage body has a generally circular outer cross section including a pair of arcuate outer surfaces arranged generally opposite one another, said cage body defining a pair of substantially planar outer surfaces arranged generally opposite one another and extending between said pair of outer arcuate surfaces; and
an expansion member slidably engaged simultaneously along said opposing pairs of inwardly tapered longitudinal edges as said expansion member is axially displaced along said longitudinal axis between said first and second shell portions to transition said cage body toward a transversely expanded configuration.

13. The implant of claim 12, wherein said first pair of longitudinal edges comprises a first pair of substantially planar longitudinal surfaces extending generally along a first plane; and
wherein said second pair of longitudinal edges comprises a second pair of substantially planar longitudinal surfaces extending generally along a second plane; and
wherein said expansion member is slidably engaged with opposing ones of said substantially planar longitudinal surfaces and axially and slidably displaced along said opposing ones of said substantially planar longitudinal surfaces to transition said cage body toward said transversely expanded configuration.

14. The implant of claim 13, wherein said first and second planes are angled relative to one another along said longitudinal axis to define an inward taper.

15. The implant of claim 12, wherein said pair of arcuate outer surfaces are threaded.

16. The implant of claim 12, wherein each of said first and second shell portions defines a transverse opening extending therethrough in communication with said hollow interior.

17. The implant of claim 16, further comprising a bone growth promoting substance positioned within said hollow interior of said cage body to facilitate bone ingrowth though said transverse openings and into said hollow interior.

18. The implant of claim 16, wherein said transverse opening has a length extending along at least about one half of an overall length of said cage body, said transverse opening having a width extending across at least about one half of an overall width of said cage body.

19. An expandable spinal implant, comprising:
a cage body extending along a longitudinal axis and including at least two movable branches having first end portions that are interconnected to one another and opposite second end portions that are movable relative to one another, said movable branches including first and second branch portions separated from one another by a longitudinal slot extending through said second end portions to a location adjacent said first end portions, wherein said first and second branch portions each have a substantially semi-cylindrical shell-like configuration and cooperate with one another to provide said cage body with a substantially cylindrical configuration having a hollow interior, said first branch portion including a first pair of substantially planar longitudinal edges defining a first hollow region therebetween, said second branch portion including a second pair of substantially planar longitudinal edges defining a second hollow region therebetween, said first hollow region of said first branch portion cooperating with said second hollow region of said second branch portion to define at least a portion of said hollow interior of said cage body, and with said first pair of substantially planar longitudinal edges arranged generally opposite said second pair of substantially planar longitudinal edges to define opposing pairs of inwardly tapered longitudinal edges extending along said longitudinal axis, at least one of said first and second branch portions defining a plurality of retention elements positioned at select axial locations along a corresponding one of said first and second pairs of substantially planar longitudinal edges; and an expansion member positioned within said slot and co-acting with said first and second branch portions to transition said cage body toward a transversely expanded configuration as said expansion member is axially displaced through said slot, said expansion member slidably engaged simultaneously along said opposing pairs of inwardly tapered longitudinal edges as said expansion member is axially displaced along said longitudinal axis between said first and second branch portions to transition said cage body toward said transversely expanded configuration, said expansion member engaged with at least one of said retention elements to retain said expansion member at a select axial location between said first and second branch portions and to maintain said cage body in said transversely expanded configuration.

20. The implant of claim 19, wherein said retention elements comprise ratchets.

21. The implant of claim 20, wherein each of said first and second branch portions defines a plurality of said retention elements positioned at select axial locations along said first and second pairs of substantially planar longitudinal edges.

22. The implant of claim 19, wherein said first and second pairs of substantially planar longitudinal edges are arranged transversely opposite one another; and wherein said first pair of substantially planar longitudinal edges extends generally along a first plane, said second pair of substantially planar longitudinal edges extending generally along a second plane, said first and second planes angled relative to one another along said longitudinal axis to define an inward taper.

23. The implant of claim 19, wherein said cage body includes a pair of arcuate outer surfaces arranged generally opposite one another, said cage body defining a pair of substantially planar outer surfaces arranged generally opposite one another and extending between said pair of outer arcuate surfaces.

24. The implant of claim 23, wherein said pair of arcuate outer surfaces are threaded.

25. The implant of claim 19, wherein each of said first and second branch portions defines a transverse opening extending therethrough in communication with a hollow interior of said cage body; and the implant further comprising a bone growth promoting substance positioned within said hollow interior of said cage body to facilitate bone ingrowth though said transverse openings and into said hollow interior.

26. The implant of claim 19, wherein said second end portions of said movable branches are configured to provide said cage body with a bullet-shaped leading end portion to facilitate insertion of said cage body between adjacent vertebral bodies.

27. The implant of claim 19, wherein each of said first and second pairs of substantially planar longitudinal edges extends from an outer surface of said cage body to said hollow interior of said cage body.

* * * * *

UNITED STATES PATENT AND TRADEMARK OFFICE
CERTIFICATE OF CORRECTION

PATENT NO. : 7,655,046 B2
APPLICATION NO. : 11/335261
DATED : February 2, 2010
INVENTOR(S) : Dryer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 445 days.

Signed and Sealed this

Twenty-third Day of November, 2010

David J. Kappos
*Director of the United States Patent and Trademark Office*